United States Patent
Luo

(10) Patent No.: US 11,430,959 B2
(45) Date of Patent: Aug. 30, 2022

(54) THERMALLY ACTIVATED DELAYED FLUORESCENCE MATERIAL AND ORGANIC LIGHT-EMITTING DIODE PREPARED USING SAME

(71) Applicant: WUHAN CHINA STAR OPTOELECTRONICS SEMICONDUCTOR DISPLAY TECHNOLOGY CO., LTD., Hubei (CN)

(72) Inventor: Jiajia Luo, Hubei (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 396 days.

(21) Appl. No.: 16/652,422

(22) PCT Filed: Feb. 13, 2020

(86) PCT No.: PCT/CN2020/075113
§ 371 (c)(1),
(2) Date: Mar. 31, 2020

(87) PCT Pub. No.: WO2021/098049
PCT Pub. Date: May 27, 2021

(65) Prior Publication Data
US 2021/0159425 A1    May 27, 2021

(30) Foreign Application Priority Data
Nov. 22, 2019   (CN) .......................... 201911156722.5

(51) Int. Cl.
*H01L 51/00*   (2006.01)
*C09K 11/06*   (2006.01)
*C07D 495/04*   (2006.01)
*H01L 51/50*   (2006.01)

(52) U.S. Cl.
CPC ........ *H01L 51/0074* (2013.01); *C07D 495/04* (2013.01); *C09K 11/06* (2013.01); *H01L 51/0071* (2013.01); *H01L 51/0072* (2013.01); *C09K 2211/1018* (2013.01); *H01L 51/5016* (2013.01)

(58) Field of Classification Search
CPC ............. H01L 51/0074; H01L 51/0071; H01L 51/0072; H01L 51/5016; H01L 51/5012; H01L 51/0061; C07D 495/04; C09K 11/06; C09K 2211/1018
USPC .......................................................... 257/40
See application file for complete search history.

(56) References Cited

U.S. PATENT DOCUMENTS

| | | | | |
|---|---|---|---|---|
| 10,826,007 B2 * | 11/2020 | Luo | ..................... | H01L 51/5012 |
| 11,081,654 B2 * | 8/2021 | Luo | ..................... | H01L 51/0094 |
| 11,201,289 B2 * | 12/2021 | Luo | ..................... | C09K 11/06 |
| 11,205,756 B2 * | 12/2021 | Luo | ..................... | H01L 51/0067 |
| 11,220,627 B2 * | 1/2022 | Luo | ..................... | H01L 51/0072 |
| 11,271,176 B2 * | 3/2022 | Luo | ..................... | C09K 11/06 |
| 11,279,873 B2 * | 3/2022 | Luo | ..................... | C07D 401/12 |
| 11,283,029 B2 * | 3/2022 | Bai | ..................... | H01L 51/0036 |

FOREIGN PATENT DOCUMENTS

| | | | | |
|---|---|---|---|---|
| CN | 109111488 A * | 1/2019 | .......... | C07F 15/0033 |
| KR | 20190000829 A * | 1/2019 | .......... | C07F 15/0033 |

* cited by examiner

*Primary Examiner* — Douglas J McGinty
(74) *Attorney, Agent, or Firm* — Mark M. Friedman

(57) ABSTRACT

The present disclosure provides a thermally activated delayed fluorescence material having a structure of formula (I) and having a low single-triplet energy gap, a high reverse intersystem crossover constant, and a high photoluminescence quantum yield.

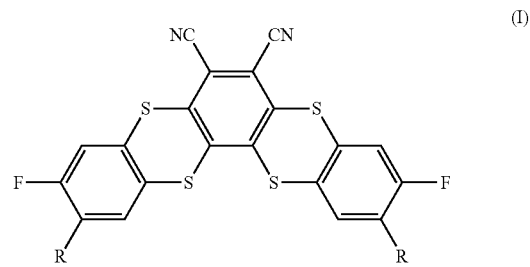

Furthermore, the present disclosure provides an organic light emitting diode including an anode, a cathode, and a light emitting layer disposed between the anode and the cathode. The light emitting layer includes the thermally activated delayed fluorescence material having the structure of formula (I).

8 Claims, 2 Drawing Sheets

THERMALLY ACTIVATED DELAYED FLUORESCENCE MATERIAL AND ORGANIC LIGHT-EMITTING DIODE PREPARED USING SAME

FIELD OF INVENTION

The present disclosure relates to the technical field of organic light-emitting materials, and particularly to a thermally activated delayed fluorescence material and an organic light-emitting diode prepared using the same.

BACKGROUND

Organic light-emitting diodes (OLEDs) have broad application prospects in fields of solid-state lighting devices and flat panel displays, and light-emitting guest materials are main factors affecting light-emitting efficiency of the organic light-emitting diodes. In the prior art, a light-emitting guest material used in an organic light-emitting diode is a fluorescence material, and its ratio of singlet exciton and triplet exciton in the organic light-emitting diode is 1:3. Therefore, in theory, internal quantum efficiency (IQE) of the organic light-emitting diode can only achieve 25%, which limits application of a fluorescent electroluminescent device. Furthermore, due to spin-orbit coupling of heavy atoms, heavy metal complex phosphorescence materials can use both singlet and triplet excitons at a same time to achieve 100% internal quantum efficiency. However, in general, heavy metals used in the heavy metal complex phosphorescent light-emitting materials are precious metals such as iridium (Ir) and platinum (Pt), and heavy metal complex phosphorescence materials need to be improved in terms of blue light-emitting materials. A purely organic thermally activated delayed fluorescence (TADF) material has a low singlet-triplet energy gap (ΔEST). Therefore, triplet excitons can return to singlet state through reverse intersystem crossing (RISC), and then radiatively transit to ground state to emit light. That is, the TADF material can use both singlet and triplet excitons at s same time and theoretically can achieve 100% internal quantum efficiency.

Thermally activated delayed fluorescence materials have low singlet-triplet energy gaps, high reverse intersystem crossover constants (kRISCs) and high photoluminescence quantum yields (PLQYs), so they have become necessary for preparation of highly efficient organic light-emitting diodes. However, current thermally activated delayed fluorescence materials with the above advantages are still relatively scarce compared to heavy metal complexes. Therefore, it is necessary to provide a novel thermally activated delayed fluorescence material to solve the problem existing in the prior art.

SUMMARY OF DISCLOSURE

In order to solve the problem, the present disclosure provides a thermally activated delayed fluorescence material having a structure of formula (I):

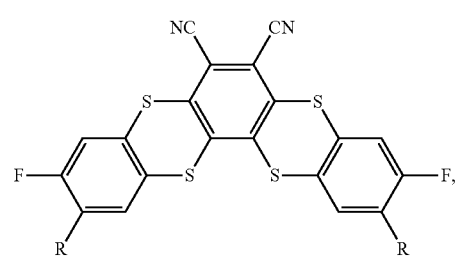

wherein R is selected from

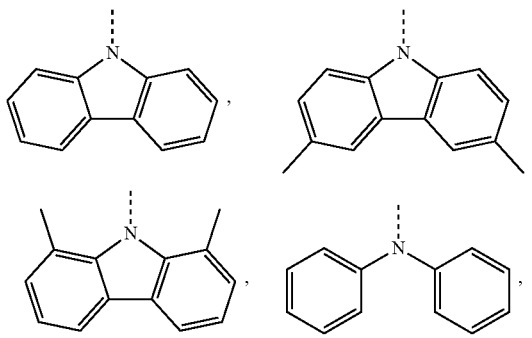

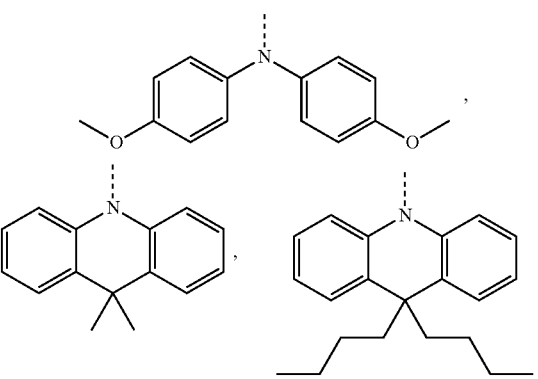

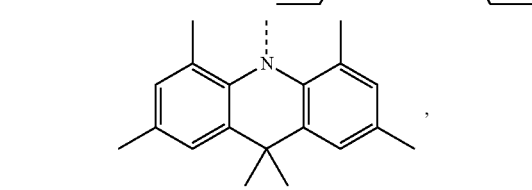

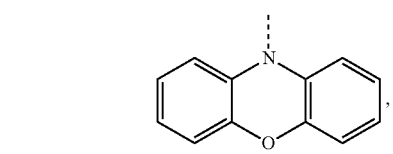

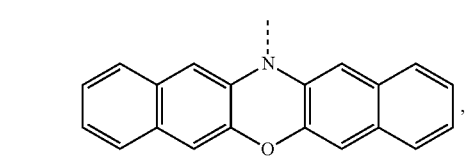

-continued

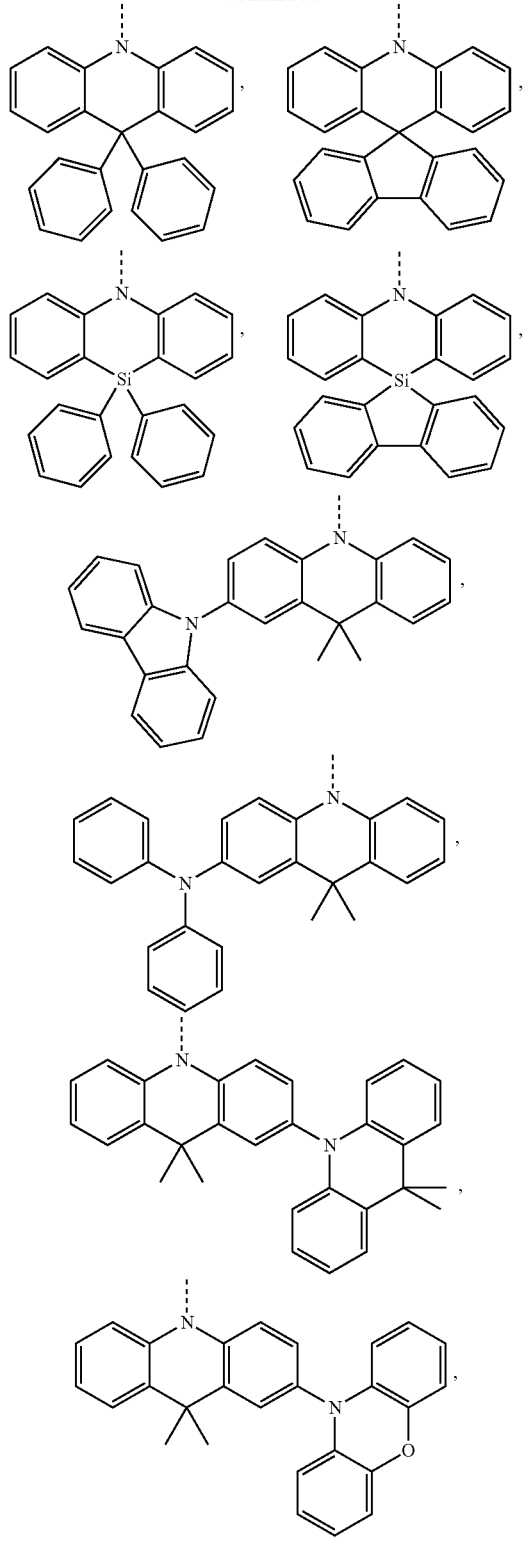

and a combination thereof.

The present disclosure further provides an organic light-emitting diode comprising an anode, a cathode, and a light-emitting layer disposed between the anode and the cathode. The light-emitting layer comprises the aforementioned thermally activated delayed fluorescence material.

In an embodiment, the thermally activated delayed fluorescence material is the following compound 1:

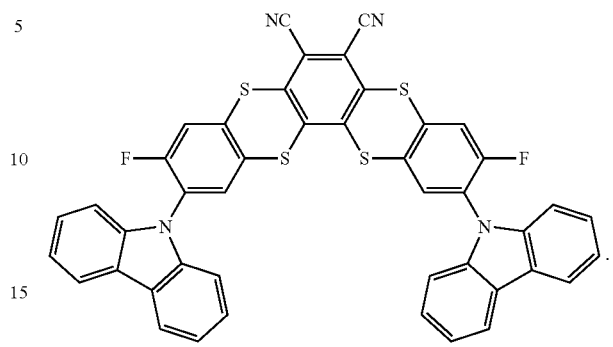

In an embodiment, compound 1 is synthesized by the following route:

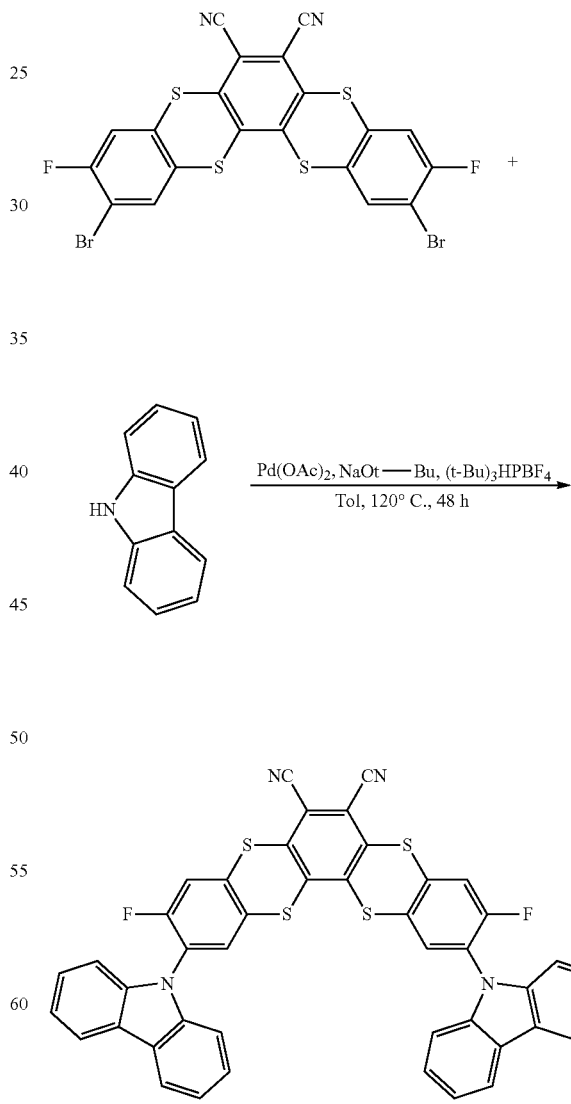

In an embodiment, the thermally activated delayed fluorescence material is the following compound 2:

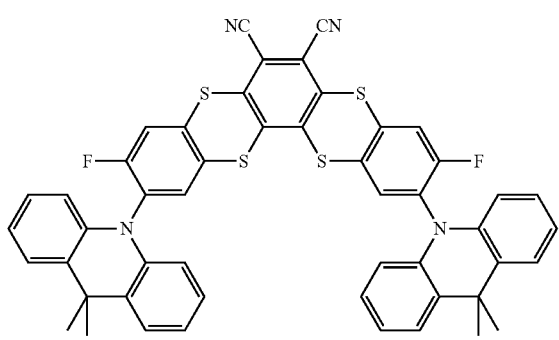

In an embodiment, compound 2 is synthesized by the following route:

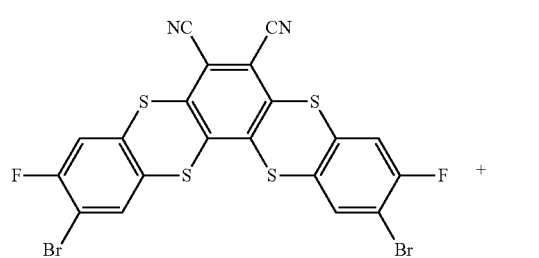

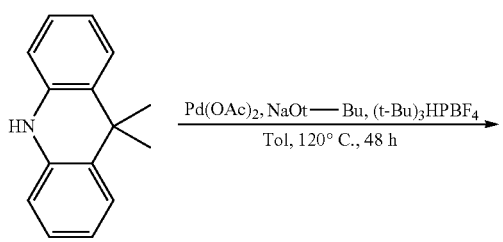

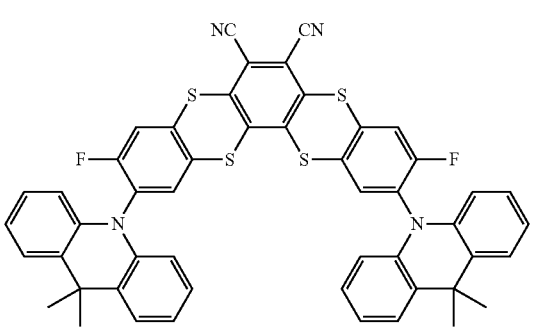

In an embodiment, the thermally activated delayed fluorescence material is the following compound 3:

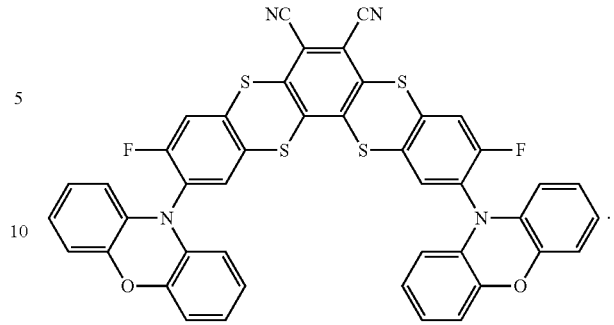

In an embodiment, compound 3 is synthesized by the following route:

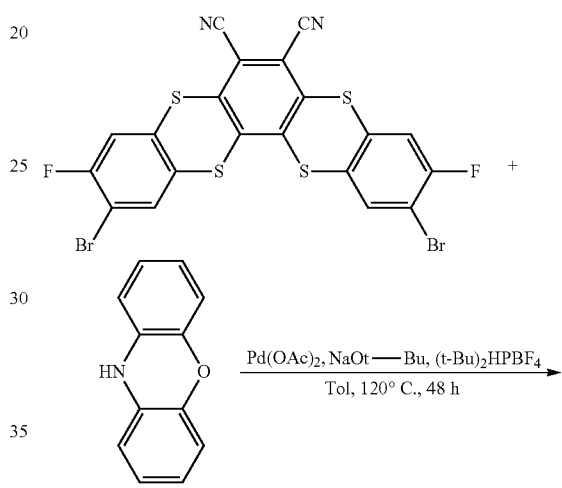

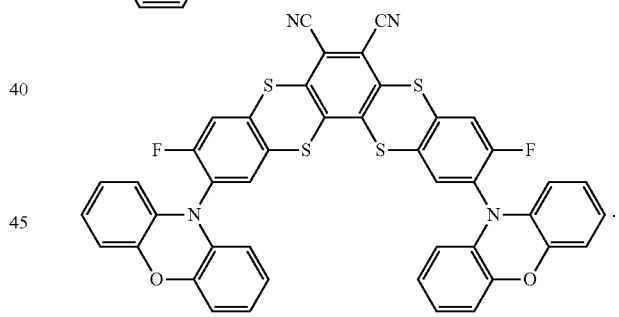

Compared with the prior art, the thermally activated delayed fluorescence material provided by the present disclosure has a lower singlet-triplet energy gap, a higher reverse intersystem crossover constant, and a higher photoluminescence quantum yield, which is beneficial for realizing an organic light-emitting diode with high light-emitting efficiency.

BRIEF DESCRIPTION OF DRAWINGS

In order to more clearly illustrate technical solutions in embodiments of the present disclosure, a brief description of accompanying drawings used in the description of the embodiments of the present disclosure will be given below. Obviously, the accompanying drawings in the following description are merely some embodiments of the present disclosure. For those skilled in the art, other drawings may be obtained from these accompanying drawings without creative labor.

DETAILED DESCRIPTION

Figure 1:
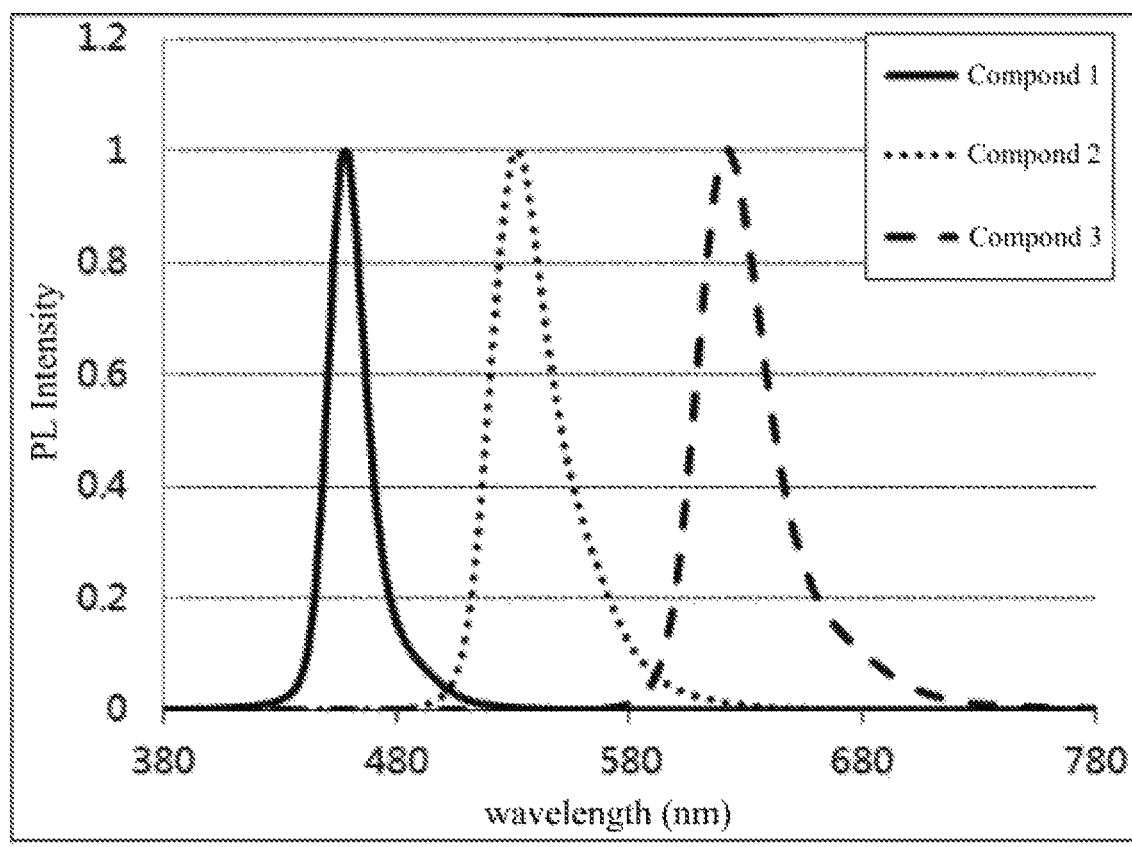
FIG. 1 is a photoluminescence spectrum of thermally activated delayed fluorescence materials according to embodiments of the present invention in a toluene solution at room temperature.

Generally, a thermally activated delayed fluorescence material has a molecular structure in which an electron donor and an electron acceptor are combined. By adjusting a structure of an electron donor to change its electron-donating ability, the present invention effectively increases high light-emitting efficiency of a thermally activated delayed fluorescence material, thereby facilitating realization of organic light-emitting diodes with high performance. The present invention provides a thermally activated delayed fluorescence material mainly having a structure of formula (I):

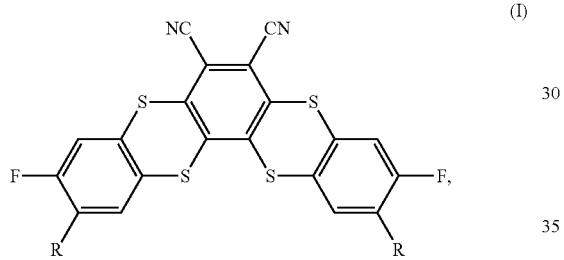

wherein R is selected from

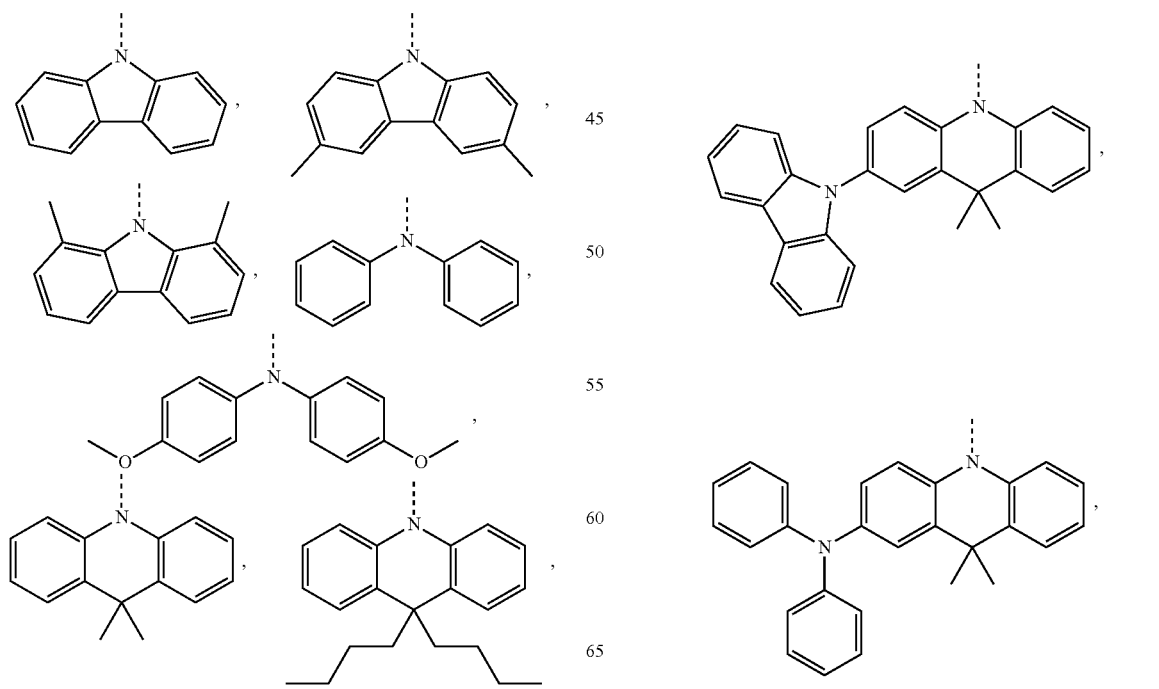

-continued

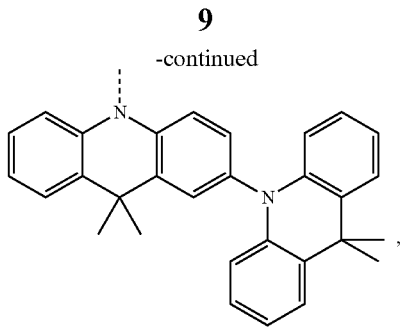

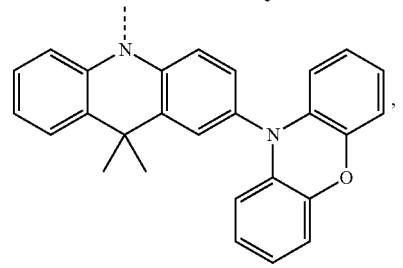

and a combination thereof. The left R group and the right R group of the structure of formula (I) are preferably same substituents, but may also be different substituents.

The present invention is described in further detail below with reference to examples and the accompanying drawings. The examples are intended to help better understand the present invention, but are not intended to limit the scope of the present invention.

Example 1: Preparation of a thermally activated delayed fluorescence material, which is Compound 1 having a structure of the following formula:

Compound 1

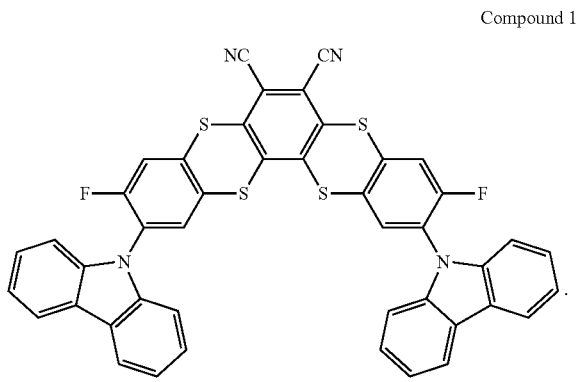

Compound 1 is synthesized by the following route:

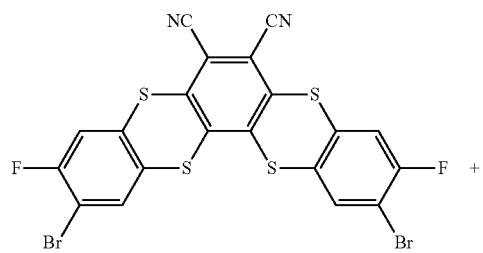

raw material 1

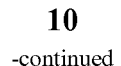

$$\xrightarrow{\text{Pd(OAc)}_2, \text{NaOt-Bu}, (t\text{-Bu})_3\text{HPBF}_4}{\text{Tol}, 120° \text{C.}, 48 \text{ h}}$$

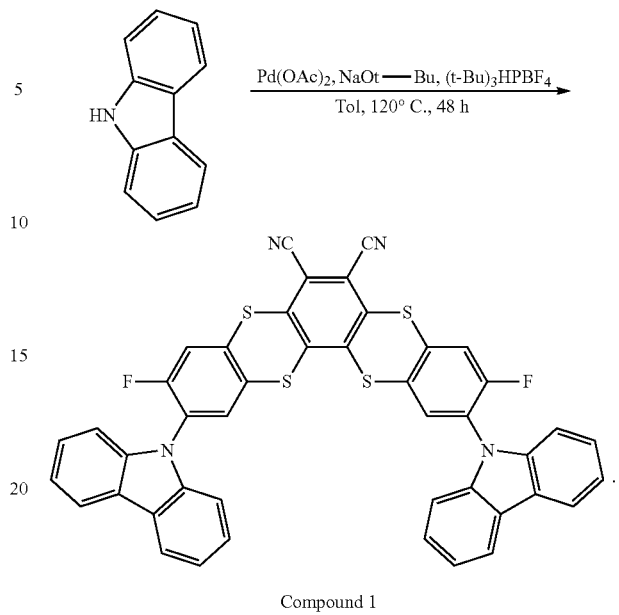

Compound 1

First, a raw material 1 (3.0 g, 5 mmol), carbazole (2.0 g, 12 mmol), palladium acetate (90 mg, 0.4 mmol), and tri-t-butylphosphine tetrafluoroborate (0.34 g, 1.2 mmol) are added in a 250 mL two-necked flask. Then, the two-necked flask is placed into a glove box, and NaOt-Bu (1.16 g, 12 mmol) is added to the two-necked flask. And then, 100 mL of toluene previously dehydrated and deoxidized is added into the two-necked flask in an argon atmosphere. The two-necked flask is placed at 120° C. for 48 hours to obtain a reaction solution. The reaction solution in the two-necked flask is cooled to room temperature, and then poured into 300 mL of ice water. Subsequently, the reaction solution is extracted with dichloromethane. After three extractions, organic phases obtained from the three extractions are combined, and then are separated and purified by column chromatography (dichloromethane:n-hexane, v:v, 1:2) to obtain the target Compound 1 (light blue powder) 2.1 g, yield 55%. MS (EI) m/z: 770.01.

Example 2: Preparation of a thermally activated delayed fluorescence material, which is Compound 2 having a structure of the following formula:

Compound 2

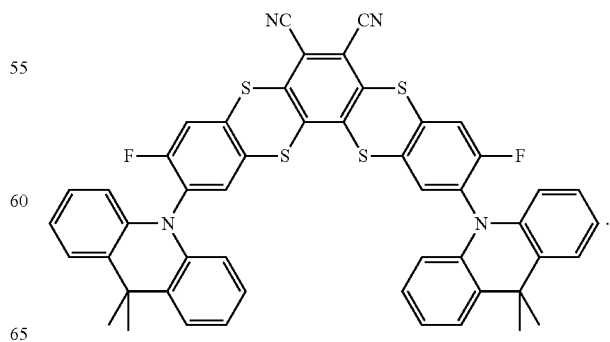

Compound 2 is synthesized by the following route:

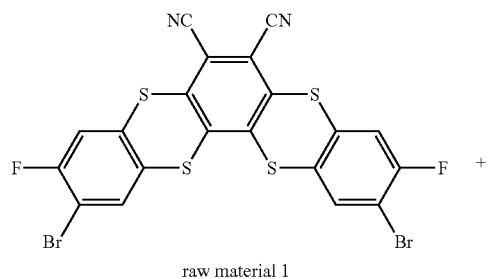

raw material 1

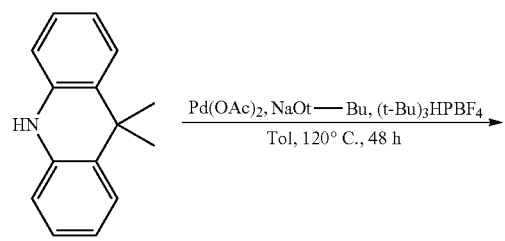

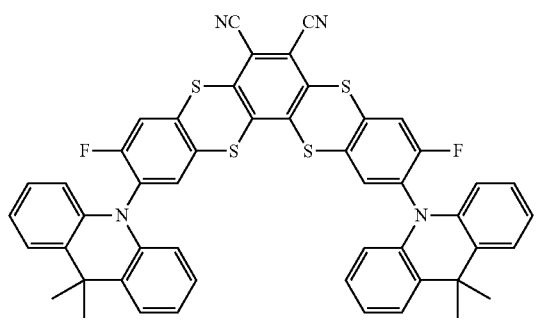

Compound 1

First, a raw material 1 (3.0 g, 5 mmol), 9,9-dimethylacridine (2.5 g, 12 mmol), palladium acetate (90 mg, 0.4 mmol), and tri-t-butylphosphine tetrafluoroborate (0.34 g, 1.2 mmol) are added in a 250 mL two-necked flask. Then, the two-necked flask is placed into a glove box, and NaOt-Bu (1.16 g, 12 mmol) is added to the two-necked flask. And then, 100 mL of toluene previously dehydrated and deoxidized is added into the two-necked flask in an argon atmosphere. The two-necked flask is placed at 120° C. for 48 hours to obtain a reaction solution. The reaction solution in the two-necked flask is cooled to room temperature, and then poured into 300 mL of ice water. Subsequently, the reaction solution is extracted with dichloromethane. After three extractions, organic phases obtained from the three extractions are combined, and then are separated and purified by column chromatography (dichloromethane:n-hexane, v:v, 2:3) to obtain the target Compound 2 (green powder) 2.0 g, yield 47%. MS (EI) m/z: 854.10.

Example 3: Preparation of a thermally activated delayed fluorescence material, which is Compound 3 having a structure of the following formula:

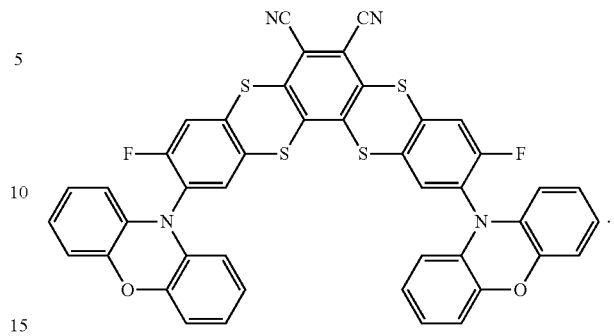

Compound 3

Compound 3 is synthesized by the following route:

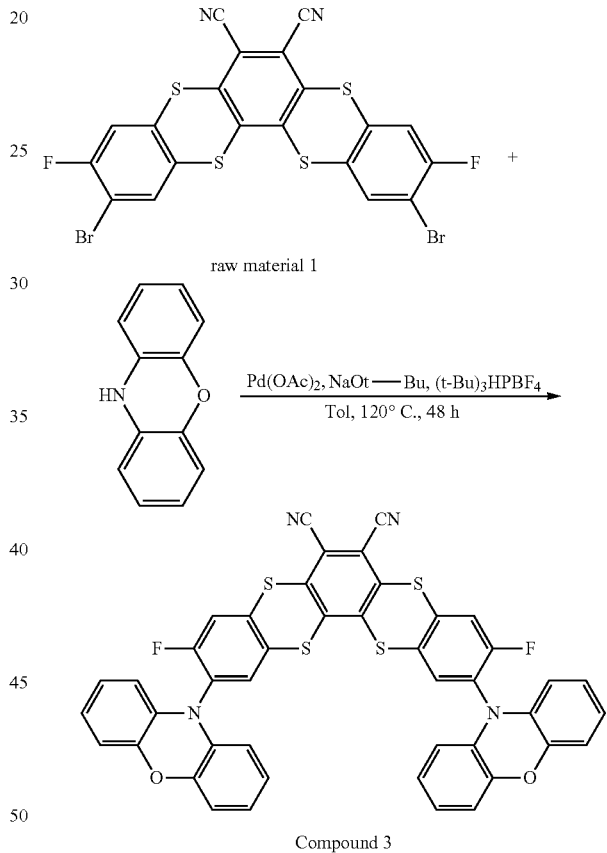

Compound 3

First, a raw material 1 (3.0 g, 5 mmol), phenoxazine (2.2 g, 12 mmol), palladium acetate (90 mg, 0.4 mmol), and tri-t-butylphosphine tetrafluoroborate (0.34 g, 1.2 mmol) are added in a 250 mL two-necked flask. Then, the two-necked flask is placed into a glove box, and NaOt-Bu (1.16 g, 12 mmol) is added to the two-necked flask. And then, 100 mL of toluene previously dehydrated and deoxidized is added into the two-necked flask in an argon atmosphere. The two-necked flask is placed at 120° C. for 48 hours to obtain a reaction solution. The reaction solution in the two-necked flask is cooled to room temperature, and then poured into 300 mL of ice water. Subsequently, the reaction solution is extracted with dichloromethane. After three extractions, organic phases obtained from the three extractions are combined, and then are separated and purified by column chromatography (dichloromethane:n-hexane, v:v, 1:1) to obtain the target Compound 3 (red powder) 1.8 g, yield 45%. MS (EI) m/z: 801.98.

Physical Properties of Compounds 1-3

The following physical properties of Compounds 1-3 are shown in Table 1: photoluminescence peak (PL peak), lowest singlet energy level (S1), lowest triplet energy level (T1), singlet-triplet energy gap (ΔEST), energy level of highest occupied molecular orbital (HOMO), and energy level of lowest unoccupied molecular orbital (LUMO).

TABLE 1

|  | PL peak (nm) | $S_1$ (eV) | $T_1$ (eV) | $\Delta E_{ST}$ (eV) | HOMO (eV) | LUMO (eV) |
|---|---|---|---|---|---|---|
| Compound 1 | 460 | 2.70 | 2.68 | 0.12 | −5.53 | −2.64 |
| Compound 2 | 530 | 2.34 | 2.16 | 0.17 | −5.40 | −2.61 |
| Compound 3 | 612 | 2.03 | 1.83 | 0.20 | −5.21 | −2.62 |

Please refer to FIG. 1, which is a photoluminescence spectrum of thermally activated delayed fluorescence materials (i.e. Compounds 1-3) according to embodiments of the present invention in a toluene solution. The photoluminescence peaks (PL peaks) of Compounds 1-3 are 460 nm, 530 nm, and 612 nm, respectively, as shown in Table 1. That is, Compounds 1-3 are representative examples of blue light-emitting thermally activated delayed fluorescence materials, green light-emitting thermally activated delayed fluorescence materials, and red light-emitting thermally activated delayed fluorescence materials, respectively.

Preparation of Organic Light-Emitting Diode

Figure 2:
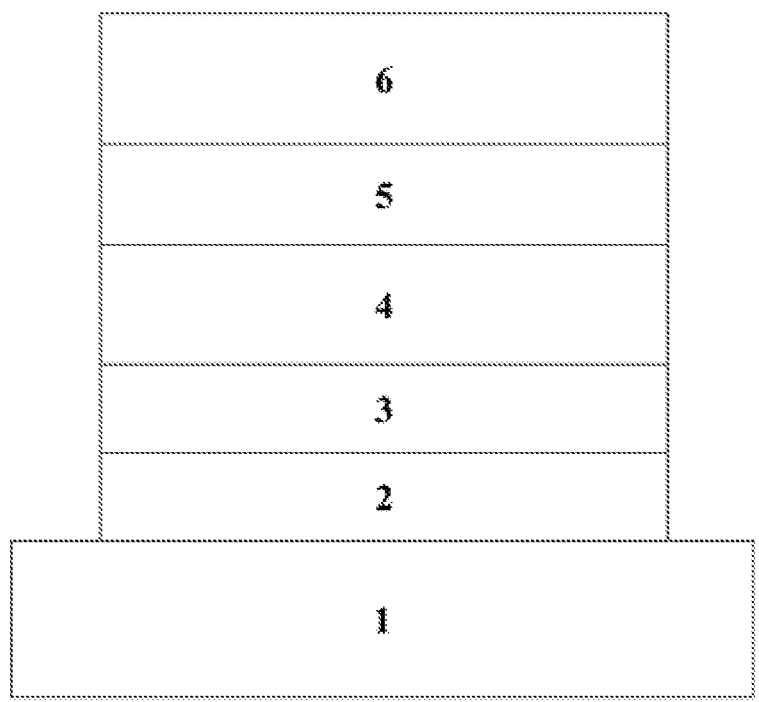
FIG. 2 is a schematic diagram of an organic light-emitting diode according to an embodiment of the present invention.

Please refer to FIG. 2, the present invention provides an organic light-emitting diode comprising a conductive glass anode layer 1, a hole injection layer 2, a hole transport layer 3, a light-emitting layer 4, an electron transport layer 5, and a cathode layer 6. Specifically, the conductive glass anode layer 1 is formed by plating a glass substrate with a layer of conductive indium tin oxide (ITO). The hole injection layer 2 is composed of molybdenum trioxide (MoO₃). The hole transport layer 3 is composed of 4,4',4"-tris(carbazol-9-yl)triphenylamine (TCTA). The light-emitting layer 4 is composed of bis[2-[(oxo)diphenylphosphino]phenyl]ether (DPEPO) and one of the thermally activated delayed fluorescence materials of the present invention. The electron transport layer 5 is composed of 1,3,5-tri[(3-pyridyl)-phen-3-yl]benzene (Tm3PyPB). The cathode layer 60 is composed of lithium fluoride and aluminum. The organic light-emitting diode may be made according to any method known in the technical field of the present invention, for example, a method disclosed in a reference "Adv. Mater. 2003, 15, 277". A specific method is: MoO₃, TCTA, DPEPO+one of the thermally activated delayed fluorescence materials (Compound 1-3), Tm3PyPB, LiF, and Al are sequentially formed on an ITO conductive glass by evaporation deposition under a high vacuum condition.

In this embodiment, Compounds 1-3 of the present invention is used to prepare organic light-emitting diodes I-III. Compositions of the organic light-emitting diodes I-III from their conductive glass anode layers 1 to the cathode layers 6 are as follows:

Organic light-emitting diode I: ITO/MoO3 (2 nm)/TCTA (35 nm)/DPEPO: Compound 1 (10%, 20 nm)/Tm3PyPB (40 nm)/LiF (1 nm)+Al (100 nm)

Organic light-emitting diode II: ITO/MoO3 (2 nm)/TCTA (35 nm)/DPEPO: Compound 2 (10% 20 nm)/Tm3PyPB (40 nm)/LiF (1 nm)+Al (100 nm)

Organic light-emitting diode III: ITO/MoO3 (2 nm)/TCTA (35 nm)/DPEPO: Compound 3 (10% 20 nm)/Tm3PyPB (40 nm)/LiF (1 nm)+Al (100 nm)

The performance data of the organic light-emitting diodes I-III are shown in Table 2. Current, brightness, and voltage of each organic light-emitting diode are measured by a Keithley source measurement system (Keithley 2400 Sourcemeter and Keithley 2000 Currentmeter) with a calibrated silicon photodiode. An electroluminescence spectrum of each organic light-emitting diodes is measured by a SPEX CCD3000 spectrometer of a French company JY. All measurements are done in a room temperature atmosphere.

TABLE 2

| OLED | Maximum current efficiency (cd/A) | Color coordinate (CIEx, CIEy) | Maximum external quantum efficiency (%) |
|---|---|---|---|
| I | 5.2 | (0.15, 0.10) | 6.3 |
| II | 66.3 | (0.22, 0.69) | 21.1 |
| III | 40.1 | (0.67, 0.29) | 15.2 |

The thermally activated delayed fluorescence materials of the examples of the present invention, comprising blue, green, and red light-emitting thermally activated delayed fluorescence materials, all have low singlet-triplet energy gaps, high reverse intersystem crossover constants, and high photoluminescence quantum yields. Furthermore, the methods for preparing the thermally activated delayed fluorescence materials provided in the examples of the present invention have high synthesis efficiency. Finally, the organic light-emitting diodes using the thermally activated delayed fluorescence materials of the examples of the present invention as the light-emitting layers have high light-emitting efficiency, and thus have long service lives, and can be applied to various display devices and electronic devices.

The present application has been described in the above preferred embodiments, but the preferred embodiments are not intended to limit the scope of the present application, and those skilled in the art may make various modifications without departing from the scope of the present application. The scope of the present application is determined by claims.

What is claimed is:

1. A thermally activated delayed fluorescence material, having a structure of formula (I):

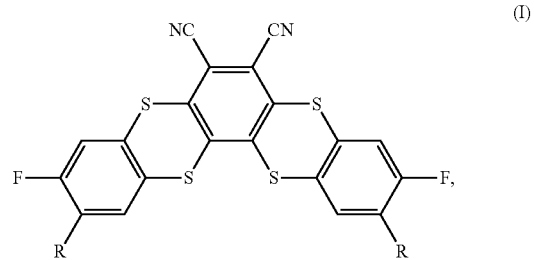

wherein R is selected from

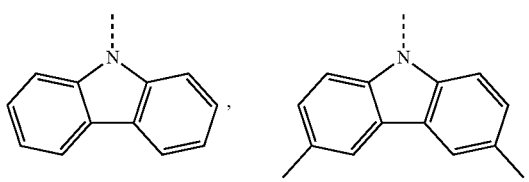

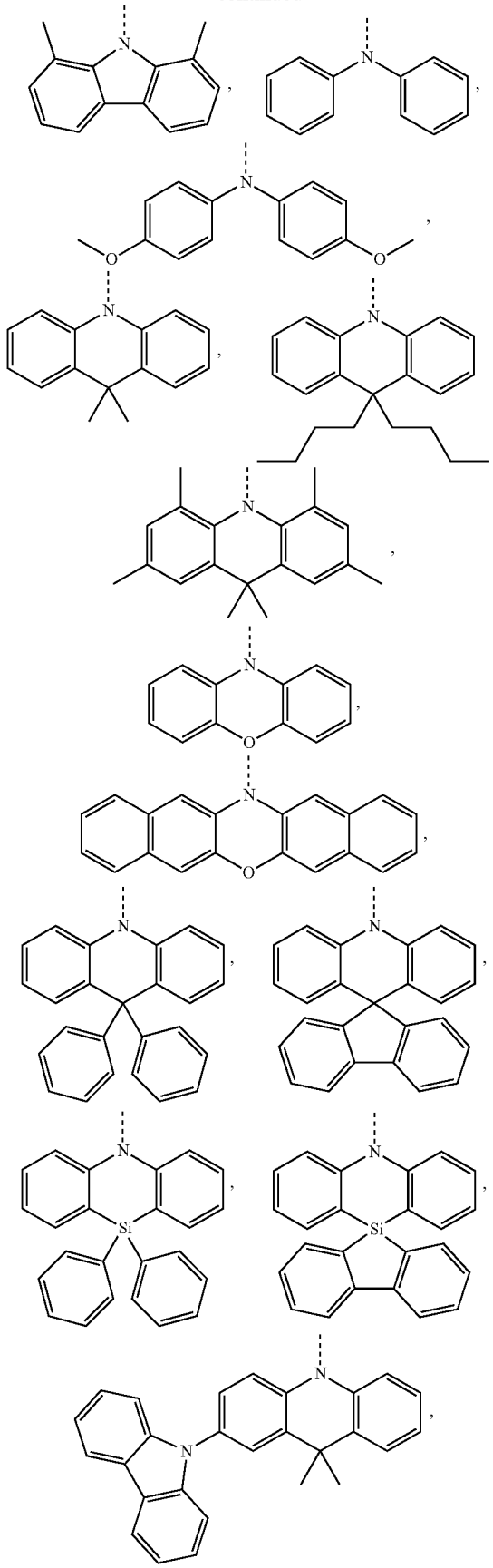
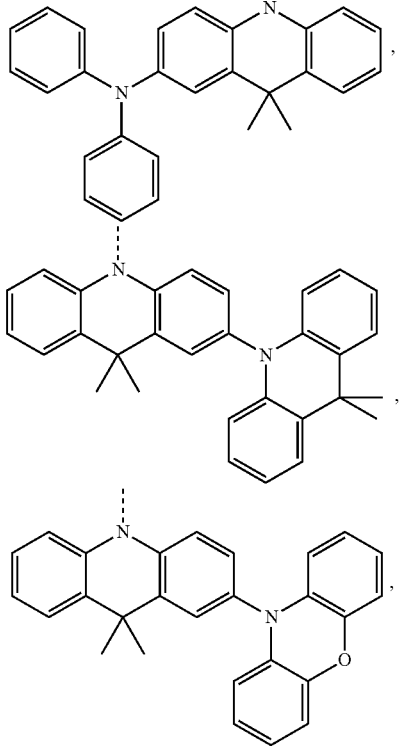
and a combination thereof.
2. The thermally activated delayed fluorescence material according to claim 1, wherein the thermally activated delayed fluorescence material is a following compound 1:
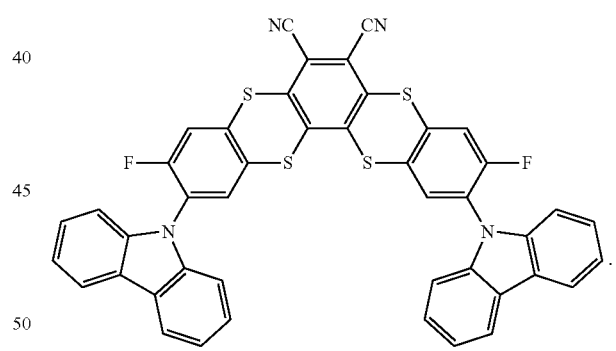
3. The thermally activated delayed fluorescence material according to claim 2, wherein the compound 1 is synthesized by a following route:
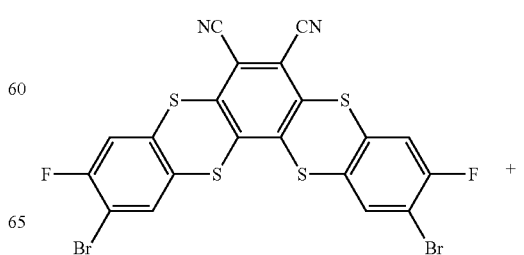 +

-continued

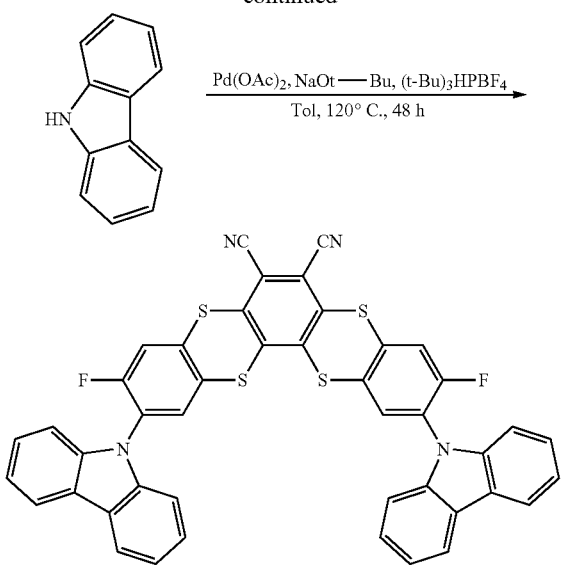

4. The thermally activated delayed fluorescence material according to claim 1, wherein the thermally activated delayed fluorescence material is a following compound 2:

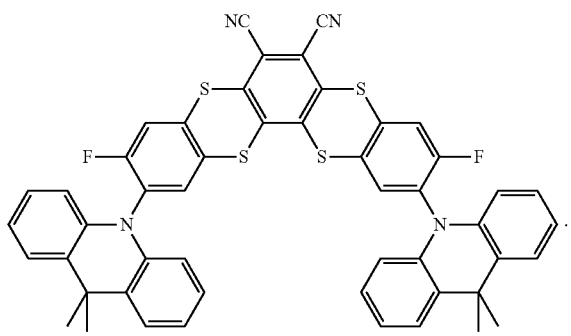 [SMILES: CC1(C)c2ccccc2N(c2cc3sc4c(sc3cc2F)c(C#N)c(C#N)c2sc3cc(F)c(N5c6ccccc6C(C)(C)c6ccccc65)cc3sc24)c2ccccc21]

5. The thermally activated delayed fluorescence material according to claim 4, wherein the compound 2 is synthesized by a following route:

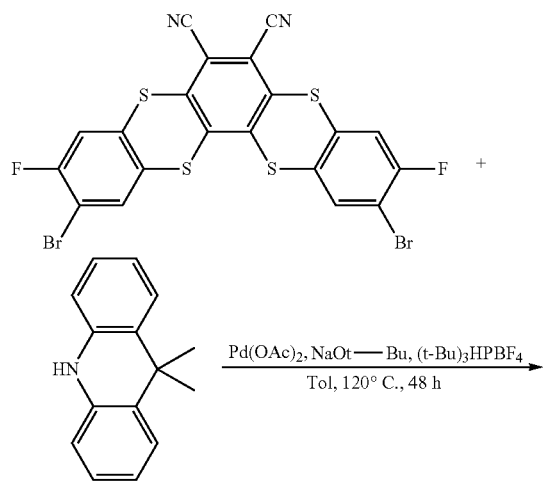

-continued

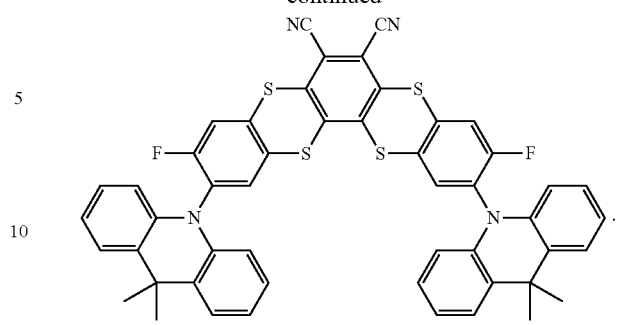

6. The thermally activated delayed fluorescence material according to claim 1, wherein the thermally activated delayed fluorescence material is a following compound 3:

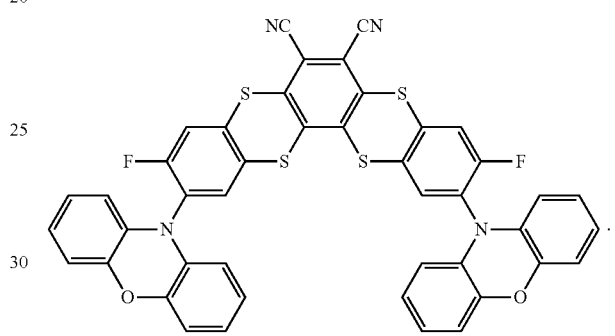

7. The thermally activated delayed fluorescence material according to claim 6, wherein the compound 3 is synthesized by a following route:

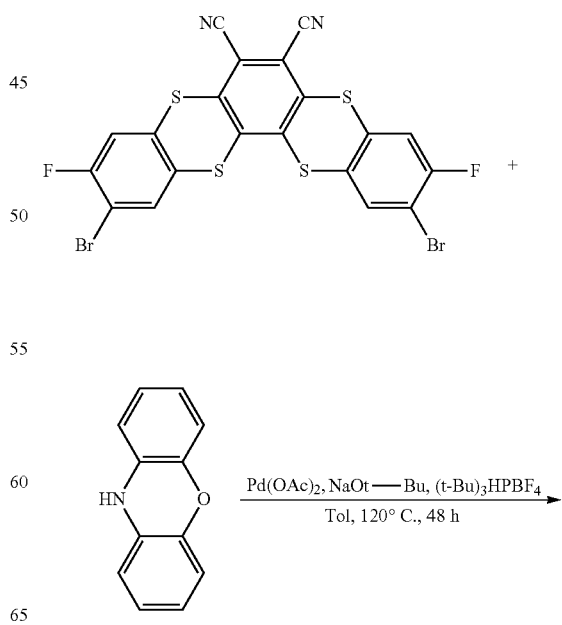

-continued
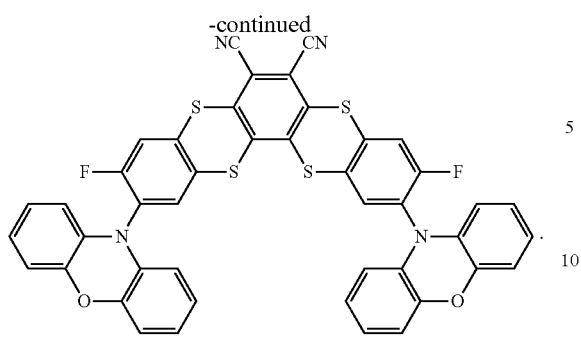
8. An organic light-emitting diode, comprising an anode, a cathode, and a light-emitting layer disposed between the anode and the cathode, wherein the light-emitting layer comprises the thermally activated delayed fluorescence material according to claim 1.
* * * * *